(12) United States Patent
Nguyen

(10) Patent No.: US 9,169,990 B2
(45) Date of Patent: Oct. 27, 2015

(54) COMPACT LOUPE LIGHT

(76) Inventor: Ronald C. Nguyen, Fountain Valley, CA (US)

(*) Notice: Subject to any disclaimer, the term of this patent is extended or adjusted under 35 U.S.C. 154(b) by 0 days.

(21) Appl. No.: 13/442,365

(22) Filed: Apr. 9, 2012

(65) Prior Publication Data

US 2013/0094217 A1  Apr. 18, 2013

Related U.S. Application Data

(63) Continuation of application No. 12/229,365, filed on Aug. 22, 2008, now Pat. No. 8,152,340.

(51) Int. Cl.
| | | |
|---|---|---|
| *F21V 5/04* | (2006.01) | |
| *G02B 25/00* | (2006.01) | |
| *G02B 19/00* | (2006.01) | |
| *G02B 25/02* | (2006.01) | |
| *A61C 1/08* | (2006.01) | |

(52) U.S. Cl.
CPC ............... *F21V 5/04* (2013.01); *G02B 19/0014* (2013.01); *G02B 19/0061* (2013.01); *G02B 25/02* (2013.01); *A61C 1/088* (2013.01); *Y10T 29/49826* (2015.01)

(58) Field of Classification Search
CPC ........... G02B 19/0004; G02B 19/0009; G02B 19/0014; G02B 19/0033; G02B 19/0047; G02B 19/0061; G02B 19/0066; G02B 25/00; G02B 25/001; G02B 25/002; G02B 25/02; A61C 1/088; Y10T 29/49826; A61B 1/06; A61B 1/0692
USPC ......... 362/186, 221, 222, 253, 265, 358, 362, 362/391, 407, 457, 116, 190, 191, 368, 362/382; 439/409, 410
See application file for complete search history.

(56) References Cited

U.S. PATENT DOCUMENTS

| | | | | |
|---|---|---|---|---|
| 1,705,465 | A * | 3/1929 | Cameron | 362/105 |
| 3,285,242 | A * | 11/1966 | Wallace | 600/249 |
| 3,739,464 | A * | 6/1973 | Eilenberger | 29/592.1 |
| 4,125,238 | A * | 11/1978 | Tanaka | 248/56 |
| 4,186,429 | A * | 1/1980 | Johnston | 362/106 |
| 4,523,259 | A * | 6/1985 | Dorsett et al. | 362/120 |
| 4,797,736 | A * | 1/1989 | Kloots et al. | 348/370 |
| 4,920,672 | A * | 5/1990 | Scott et al. | 40/363 |
| 4,967,330 | A * | 10/1990 | Bell et al. | 362/311.02 |
| 5,506,763 | A * | 4/1996 | Carley | 362/341 |
| 5,651,606 | A * | 7/1997 | Krogman | 362/96 |
| 5,667,291 | A * | 9/1997 | Caplan et al. | 362/105 |
| 6,039,461 | A * | 3/2000 | Cummings et al. | 362/287 |
| 6,078,439 | A * | 6/2000 | Silhengst et al. | 359/819 |
| 6,322,226 | B1 * | 11/2001 | Dickson | 362/33 |
| 6,457,246 | B1 * | 10/2002 | Frazer et al. | 33/286 |
| 6,594,204 | B1 * | 7/2003 | Yamamoto et al. | 369/44.14 |

(Continued)

OTHER PUBLICATIONS

Wikipedia entry, Interference fit, http://en.wikipedia.org/Interference_fit, retrieved Oct. 21, 2014.

(Continued)

*Primary Examiner* — Alan Cariaso

(57) ABSTRACT

A loupe light that is compact and lightweight is described. The loupe light includes an adhesive that is electrically insulating and thermally conducting to help secure a wire supplying power to a light source. The loupe light also includes an end piece configured to help secure the wire as well.

9 Claims, 9 Drawing Sheets

(56) References Cited

U.S. PATENT DOCUMENTS

| | | | |
|---|---|---|---|
| D491,684 S * | 6/2004 | McInnis | D26/63 |
| 6,742,913 B2 * | 6/2004 | Deutsch | 362/253 |
| 6,942,363 B1 * | 9/2005 | LeVasseur | 362/277 |
| 7,658,511 B2 * | 2/2010 | Sugiyama et al. | 362/294 |
| 8,047,684 B2 * | 11/2011 | Chang | 362/268 |
| 8,152,340 B1 * | 4/2012 | Nguyen | 362/362 |
| 2004/0090785 A1 * | 5/2004 | McInnis | 362/362 |
| 2005/0286243 A1 * | 12/2005 | Ranish et al. | 362/89 |
| 2008/0252893 A1 * | 10/2008 | Zuluaga | 356/445 |

OTHER PUBLICATIONS

Bussard, Tolerancing, http://www.maelabs.ucsd.edu/mae-guides/Tolerance/Tolerancing.htm, retrieved Oct. 21, 2014.

\* cited by examiner

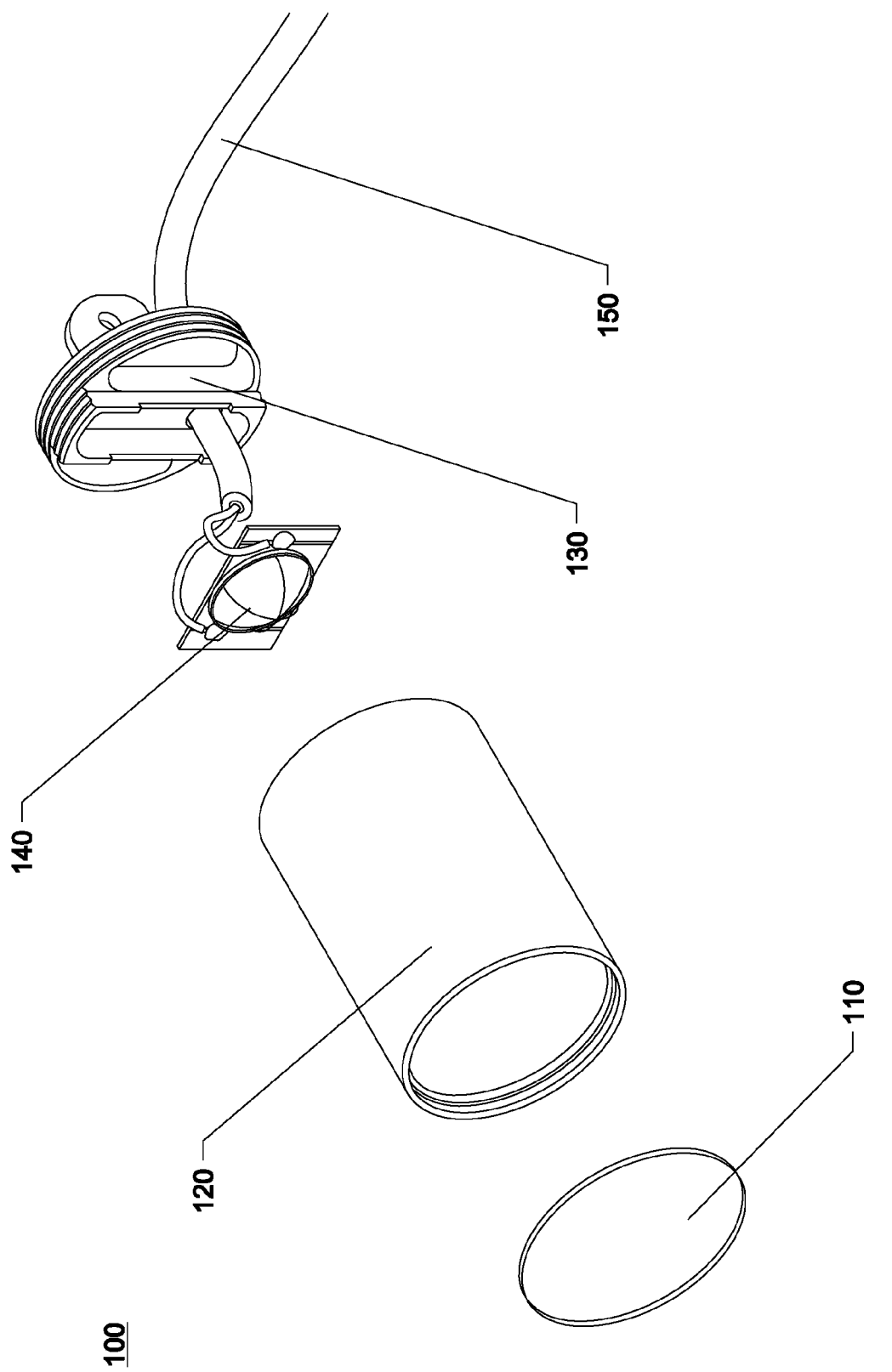

COMPACT LOUPE LIGHT

CROSS-REFERENCE TO RELATED APPLICATION

This application claims the benefit of U.S. patent application Ser. No. 12/229,365, filed Aug. 22, 2008, now U.S. Pat. No. 8,152,340, which is incorporated by reference in its entirety.

BACKGROUND

Loupe lights are lights attached to dental loupes or other eyewear to illuminate an area of interest. Some loupe lights may use a fiber optic cable that transmits light from a light source.

Loupe lights are often bulky and heavy and uncomfortable to wear for prolonged periods of time. Loupe lights may restrict movement, or cause the loupe to move or become dislodged when the user turns or moves. Loupe lights may generate large amounts of heat and become very warm with prolonged use.

Other loupe lights use a self-contained light source and draw power from a remote power supply. These loupe lights are powered by a wire. Wire protection is designed to prevent the wire from being detached from the loupe light when the wire is pulled on, either through use or by accident. Wire protection may be afforded by a knot in the wire, or a crimp or screw securing the wire.

What is needed is a loupe light that is lightweight and compact. What is also needed is a loupe light that has good wire protection.

SUMMARY

A compact loupe light is described. The compact loupe light includes a body, a lens coupled to an end of the body, and an end piece coupled to an other end of the body. The end piece has a hole and an open channel on an inside of the end piece. The hole is positioned within the channel. The compact loupe light also includes an adhesive at least partially filling the channel, and a wire having a size substantially the same as the hole, the wire having a width substantially the same as the channel, the wire passing through the hole and making a bend before passing through at least a portion of the channel, the wire being held in the channel at least partially by the adhesive. The compact loupe light also includes a light source coupled to wire.

BRIEF DESCRIPTION OF THE DRAWINGS

FIGS. 1A-1B show assembled and exploded views of one embodiment of a compact loupe light.

DETAILED DESCRIPTION OF PREFERRED EMBODIMENTS

Figure 1A:
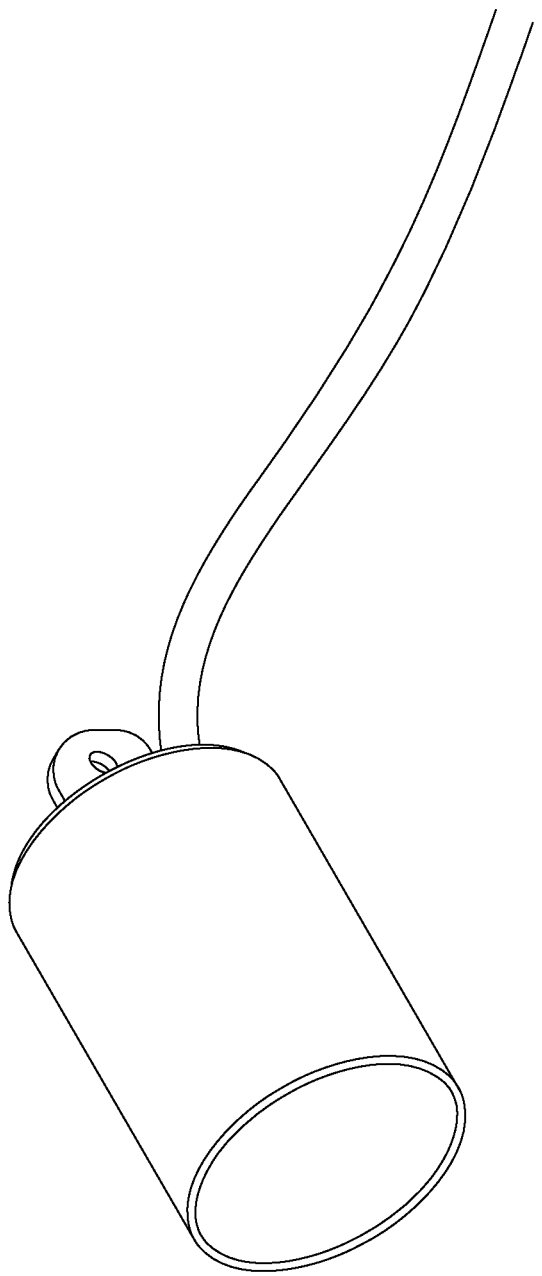

FIGS. 1A-1B show assembled and exploded views of one embodiment of a compact loupe light 100. Compact loupe light 100 includes a lens 110, a body 120, an end piece 130, a light source 140, a wire 150, and an adhesive 160.

Lens 110 may be any suitable shape or configuration, and may be manufactured out of glass, plastic, or any other suitable material. In the embodiment shown, lens 110 is a biconvex singlet lens. Lens 110 may be coupled to body 120 by a press fit, threading, adhesive, or any other suitable method of coupling. In the embodiment shown, lens 110 is press fit to a front end of body 120.

Figure 2A:
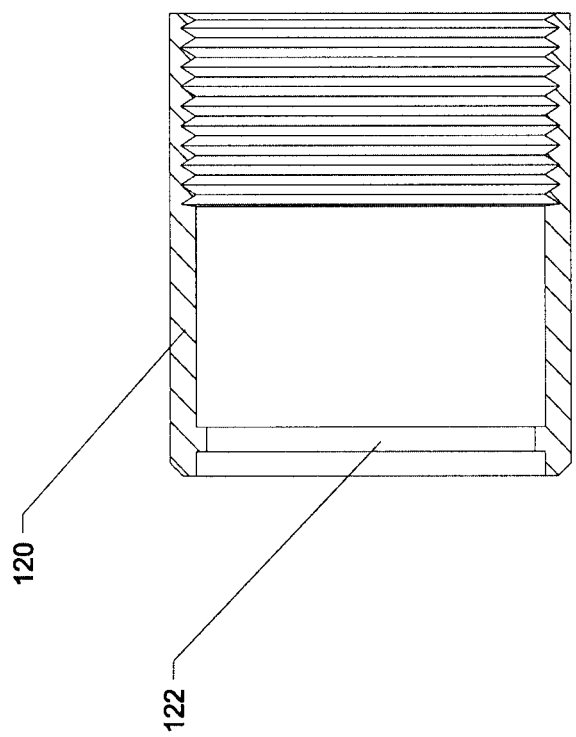
FIG. 2A shows a side cross-sectional view of one embodiment of a body of a compact loupe light.
Figure 2B:
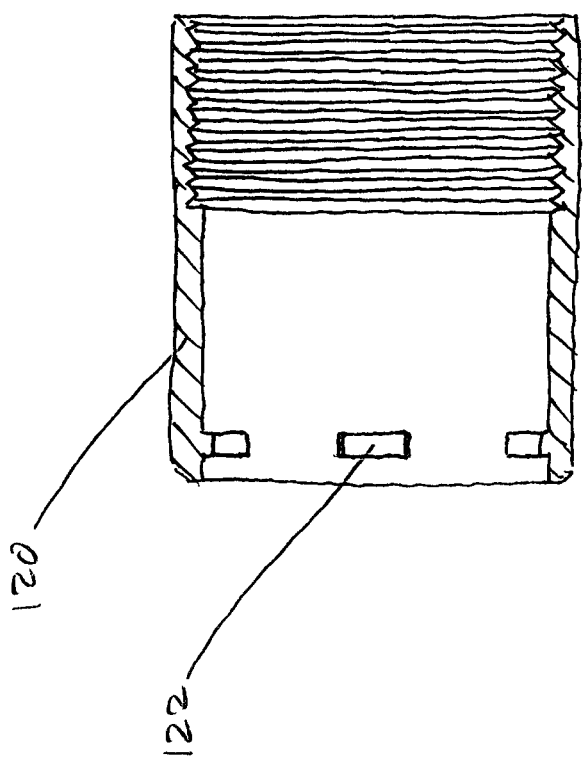
FIG. 2B shows a side cross-sectional view of another embodiment of a body of a compact loupe light.

FIGS. 2A-2B show side cross-sectional views of embodiments of a body 120 of a compact loupe light 100. Body 120 may be cylindrical, conical, partially conical or any suitable shape or configuration. In the embodiments shown, body 120 is substantially cylindrical. Body 120 may be manufactured out of metal, plastic, or any other suitable material. In one embodiment, body 120 is manufactured out of 6061 aluminum alloy. Body 120 may be anodized or otherwise colored dark to reduce glare. In the embodiments shown, the front end of body 120 may include a lens stop 122 against which lens 110 is seated. Lens stop 122 may be one or more protrusions inside body 120, as shown in FIG. 2B, or lens stop 122 may be continuous, as shown in FIG. 2A. In the embodiments shown, a rear end of body 120 is threaded to receive end piece 130.

Figure 3:
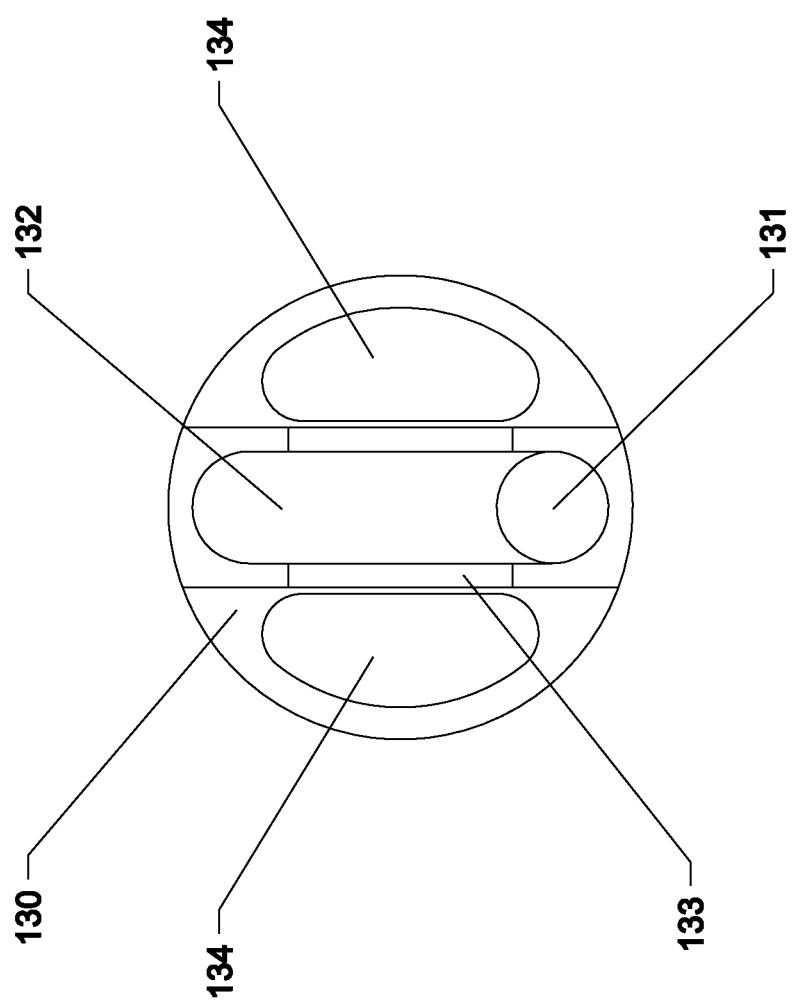
FIG. 3 shows a front view of one embodiment of an end piece of a compact loupe light.

FIG. 3 shows a front view of one embodiment of an end piece 130 of a compact loupe light 100.

End piece 130 may be any suitable shape or configuration, and may be manufactured out of metal, plastic, or any other suitable material. In the embodiment shown, end piece 130 is substantially cylindrical and is manufactured out of 6061 aluminum alloy. End piece 130 may be coupled to body 120 by press fit, threading, adhesive, or any other suitable method of coupling. In the embodiment shown, end piece 130 is threaded and configured to be coupled to the rear end of body 120, which is also threaded.

End piece 130 includes a hole 131 and an open channel 132 formed in end piece 130. Hole 131 is positioned within channel 132. In the embodiment shown, hole 131 is substantially circular and has a size substantially similar to that of wire 150. In the embodiment shown, channel 132 has a width substantially similar to that of wire 150. Channel 132 is also sufficiently deep to accommodate wire 150. Channel 132 is formed by channel walls 133. End piece 130 may have portions 134 removed to save weight.

Channel 132 may include other features which allow wire 150 to be held more securely in channel 132. For example, channel 132 may have ribs which extend partially into channel 132 and allows wire 150 to be held more securely in channel 132. As another example, channel 132 may have a surface treatment which allows wore 150 to be held more securely in channel 132.

Channel 132 may also have a cross-section which allows wire 150 to be held more securely in channel 132. Channel 132 may have cross-section that is wider at a top of channel 132 than at a bottom of channel 132. Channel 132 with this "wedge" cross-section allows wire 150 to be held more securely in channel 132 as wire 150 is pressed down into channel 132.

Figure 4A:
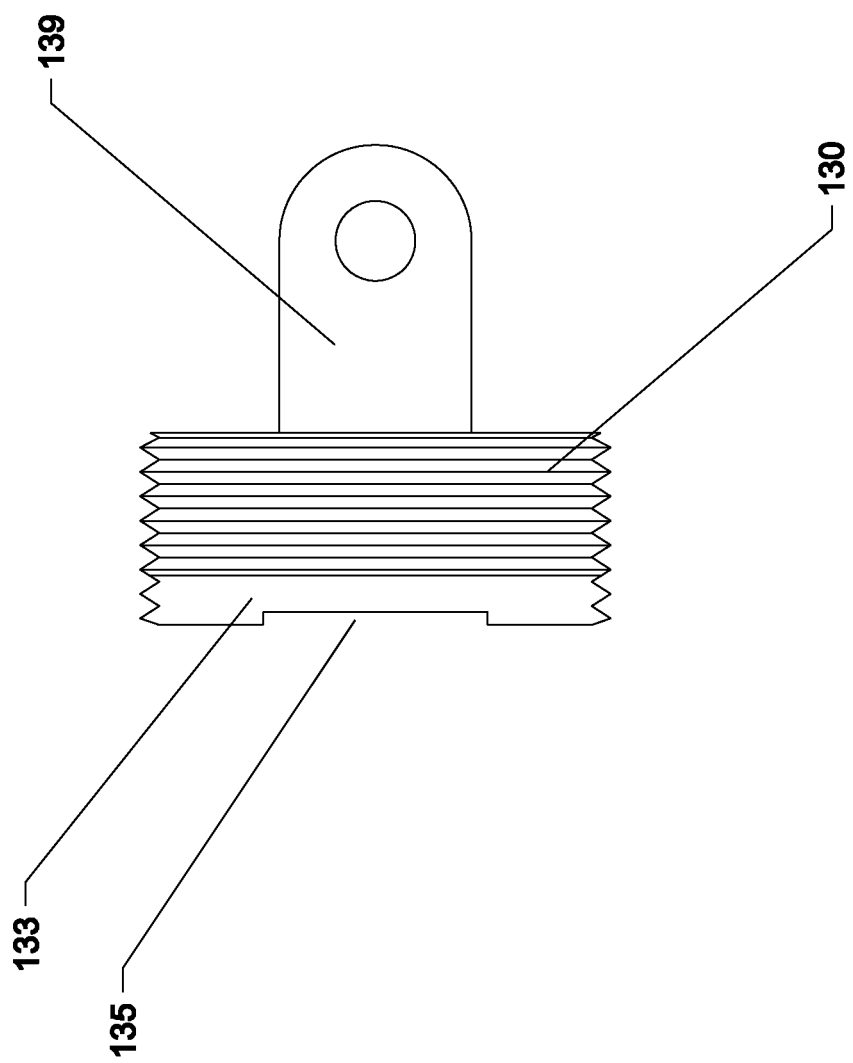
FIGS. 4A-4B show side and cross-sectional views of one embodiment of a compact loupe light.
Figure 4B:
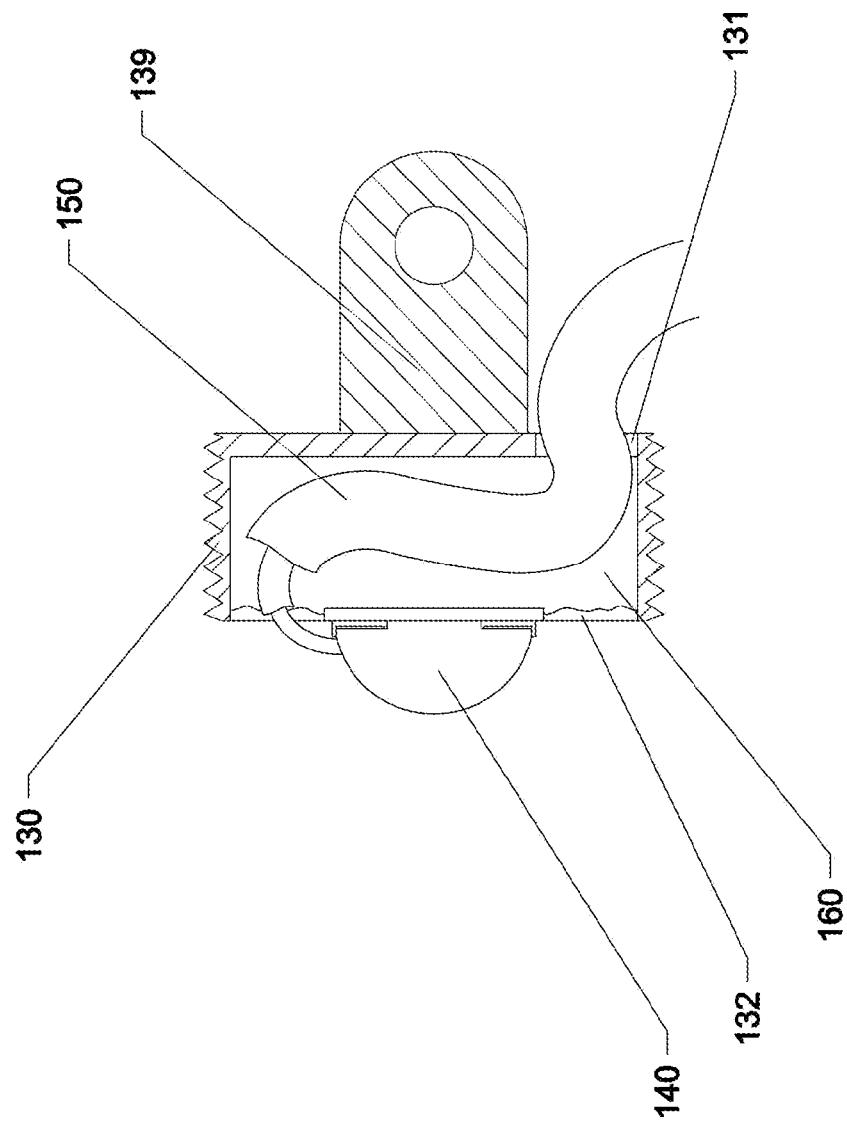
Figure 4C:
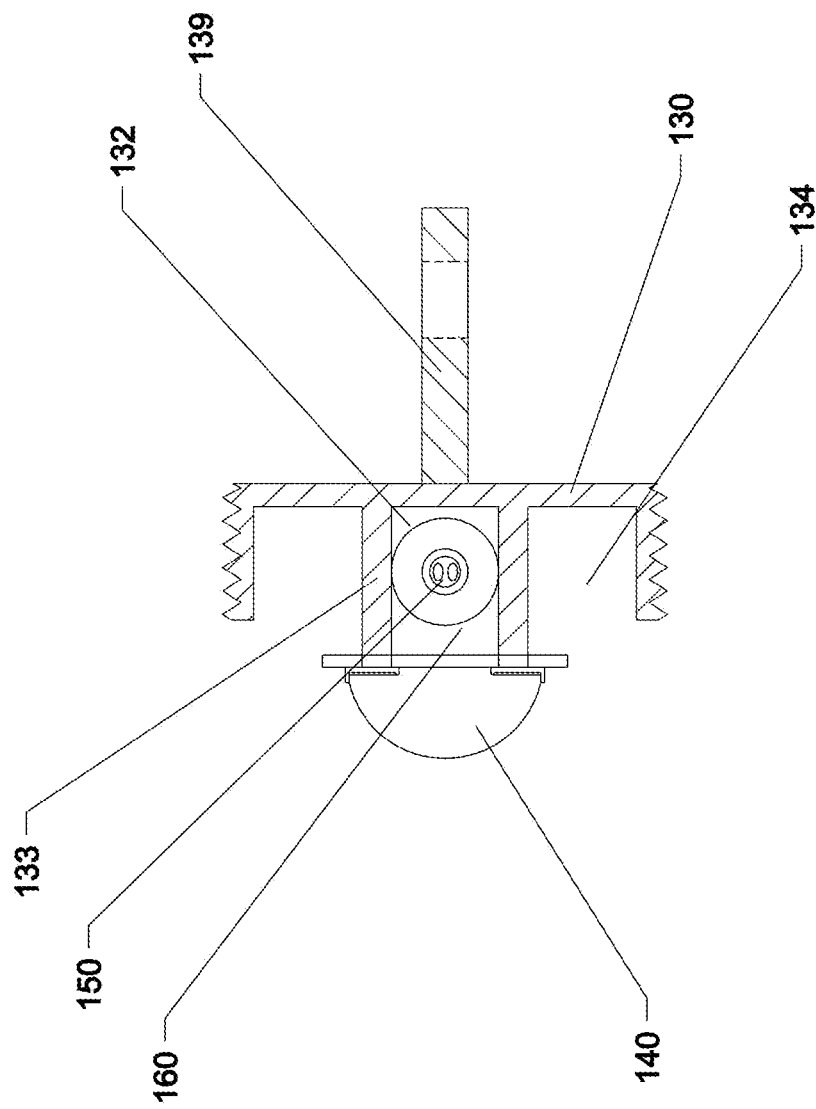

FIGS. 4A-4C show side and cross-sectional views of one embodiment of an end piece 130 of a compact loupe light 100.

Channel walls 133 may be configured to be coupled to light source 140. In the embodiment shown, channel walls 133 include indentations 135 configured to assist in properly positioning or securing light source 140.

End piece 130 may have a mounting tab 139 which facilitates the coupling of compact loupe light 100 to a loupe.

Mounting tab 139 may be used with different adapters in order to adapt compact loupe light 100 for use with different types of loupes.

Light source 140 may be any suitable source of light. In the embodiment shown, light source is an LED light mounted on a circuit board. Light source 140 may be a Cree XLamp 7090 XREWHT-L1-0000-X0D01 or a Cree XLamp 7090 XRE-WHT-L1-WH-R2-0-01.

Wire 150 may be of any suitable shape or configuration. In the embodiment shown, wire 150 is substantially cylindrical and includes two conductors and an insulating cover. Wire 150 may be coupled to light source 140 by soldering or any other suitable method of coupling. Wire 150 may be configured for connection to a power source.

Wire 150 passes through hole 131 and makes a bend before passing through at least portion of channel 132. The bend may be at least 75 degrees, but is preferably 90 degrees or greater.

Adhesive 160 at least partially fills channel 132. Adhesive 160 allows wire 150 to be held more securely in channel 132. Adhesive 160 fills channel 132 sufficiently to contact light source 140. Adhesive 160 allows light source 140 to be coupled more securely to end piece 130. Adhesive 160 may be Arctic Silver Arctic Alumina.

Adhesive 160 is electrically insulating. Electrical current from wire 150 will not conducted by adhesive 160. Adhesive 160 is also thermally conducting. Thus, waste heat from light source 140 is carried away by adhesive 160 and into end piece 130 and body 120. Adhesive 160, end piece 130, and body 120 thus act as a heat sink for light source 140.

Wire 150 is thus held in place by a combination of hole 131, channel 132, the bend created as wire passes through hole 131 and into channel 132, adhesive 160, and light source 140. This provides wire protection to wire 150 and strain relief to light source 140 in an effective and compact manner.

Figure 5:
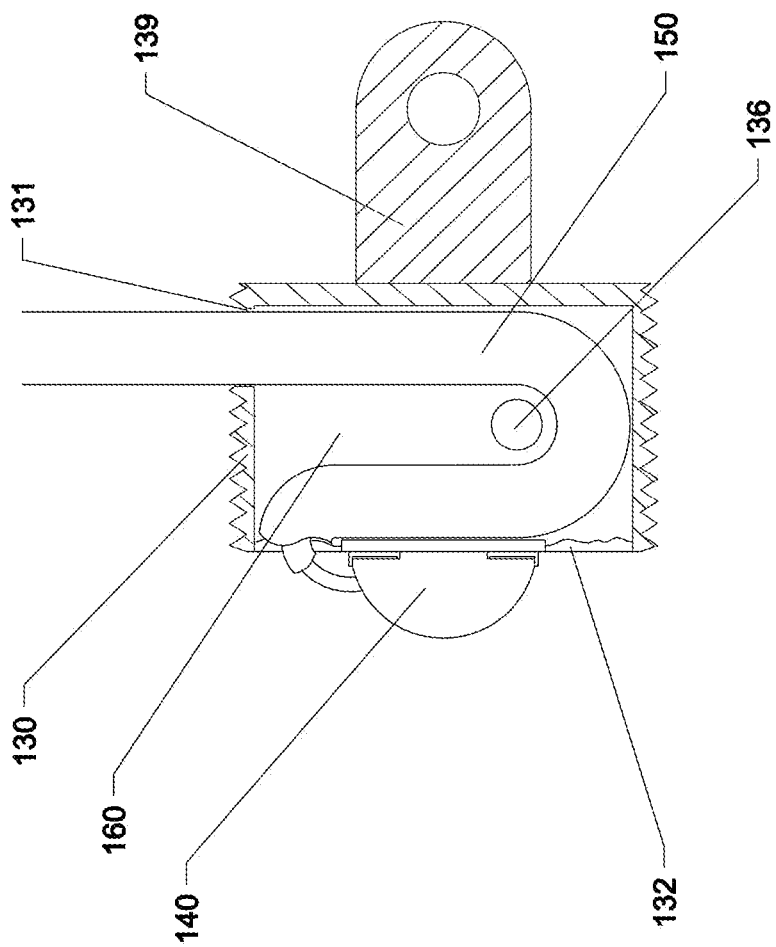
FIG. 5 shows a cross-sectional view of another embodiment of a compact loupe light.

FIG. 5 shows a cross-sectional view of another embodiment of an end piece 130 of a compact loupe light 100.

Hole 131 is positioned on a side of end piece 130. Wire 150 passes through hole 131 and at least a portion of channel 132, bends around a pin 136, and passes through another portion of channel 132.

Compact loupe light 100 can thus be made lightweight and compact. For example, compact loupe light 100 can be made to have a diameter of 0.65 inches or less, which is about the same as a dime, and a length of 0.76 inches or less. The compact loupe light 100 can be made to have a weight of 0.18 ounces or less, which is approximately the weight of a nickel.

While the invention has been described in terms of some specific examples and in some specific embodiments, it will be clear that this invention is not limited to these specific examples and embodiments and that many changes and modified embodiments will be obvious to those skilled in the art without departing from the true spirit and scope of the invention as defined in the appended claims.

What is claimed is:

1. A compact loupe light comprising:
   a body;
   a lens stop formed on an inside of the body;
   a lens coupled to a front end of the body, the lens coupled by a press fit with the inside of the body, the press fit being between the body alone and the lens, the lens being seated against the lens stop; and
   an end piece coupled to a rear end of the body, the end piece having a mounting tab, wherein the mounting tab is configured to be coupled to eyewear.

2. The compact loupe light of claim 1, wherein the body is substantially cylindrical.

3. The compact loupe light of claim 1, wherein the lens stop includes a circumferential protrusion formed on the inside of the body.

4. The compact loupe light of claim 1, wherein the lens stop includes one or more protrusions formed on the inside of the body.

5. The compact loupe light of claim 1, wherein the lens stop includes a continuous protrusion on the inside of the body.

6. The compact loupe light of claim 1, wherein the lens includes a biconvex singlet lens.

7. The compact loupe light of claim 1, wherein the lens is substantially circular.

8. The compact loupe light of claim 1, wherein the rear end of the body is threaded, and the end piece is threaded and configured to be coupled to the rear end of the body.

9. The compact loupe light of claim 1, wherein the end piece is press fit to the rear end of the body.

* * * * *